United States Patent [19]

Ghayouran

[11] 4,044,759
[45] Aug. 30, 1977

[54] AUTO-TRANSFUSION TORNIQUET APPLIANCE AND METHOD OF UTILIZING THE SAME TO CONTROL FLOW OF BLOOD THROUGH A BLOOD VESSEL

[76] Inventor: Bahman Ghayouran, 860 Harrison Ave., Boston, Mass. 02111

[21] Appl. No.: 657,212

[22] Filed: Feb. 11, 1976

[51] Int. Cl.² .............................................. A61H 1/00
[52] U.S. Cl. ................................................... 128/24 R
[58] Field of Search ............... 128/24 R, DIG. 20, 60, 128/64, 327, DIG. 15

[56] References Cited

U.S. PATENT DOCUMENTS

| | | | |
|---|---|---|---|
| 2,699,165 | 1/1955 | Ferrier | 128/60 |
| 2,781,041 | 2/1957 | Weinberg | 128/24 R |
| 3,288,132 | 11/1966 | Meredith | 128/24 R |
| 3,752,148 | 8/1973 | Schmalzbach | 128/DIG. 20 |
| 3,933,150 | 1/1976 | Kaplan et al. | 128/DIG. 20 |

*Primary Examiner*—Lawrence W. Trapp
*Attorney, Agent, or Firm*—Munroe H. Hamilton

[57] ABSTRACT

An improved surgical appliance for controlling flow of blood through blood vessels consists of a novel torniquet apparatus. Included in the torniquet apparatus is a wrapper member made up of a non-stretchable cloth or similar material, and means for firmly securing the wrapper around the leg of a patient. Contained within the wrapper are three inflatable chambers which can be supplied with a flow of compressed air to provide a means of selectively exerting pressure inside the wrapper and against blood vessels in the leg.

A lower chamber comprises a rubber tube which is initially inflated to exert localized pressure around the ankle of the patient. A second intermediate chamber is made up of layers of rubberlike material yieldably held together by a Velcro fastening material. The intermediate chamber communicates with the first chamber and the Velcro layers, in response to increasing pressures in the first chamber gradually become forced apart to allow pressure to be exerted progressively upwardly from the ankle region towards the thigh, thus forcing blood to flow out of the leg with the arteries and veins becoming collapsed. When a desired quantity of blood has been displaced along blood vessels in the upper thigh, the third chamber is activated. This chamber is separated from the lower and intermediate chambers and includes a separate rubber tubing which can be rapidly inflated to hold the veins and arteries of the upper thigh in a tightly clamped position so as to prevent a return flow of blood to the lower leg while desired operative procedures are being carried out.

4 Claims, 18 Drawing Figures

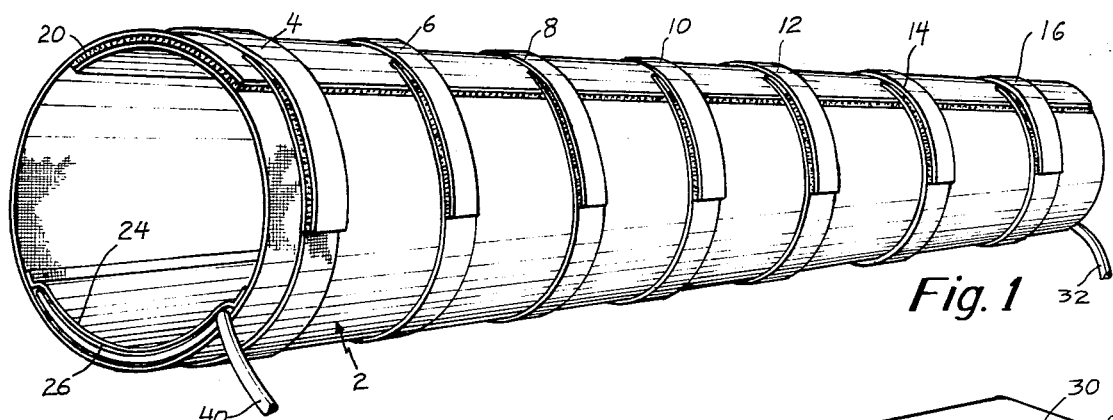
Fig. 1
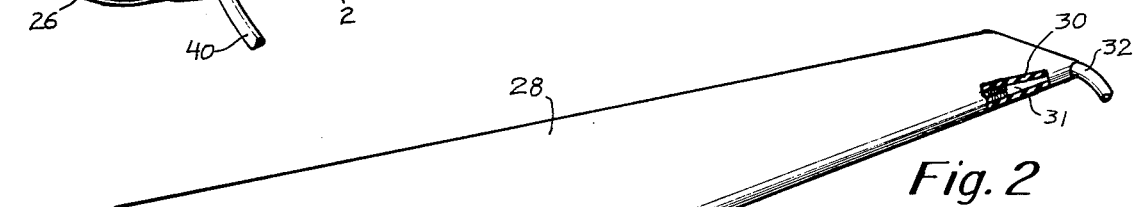
Fig. 2
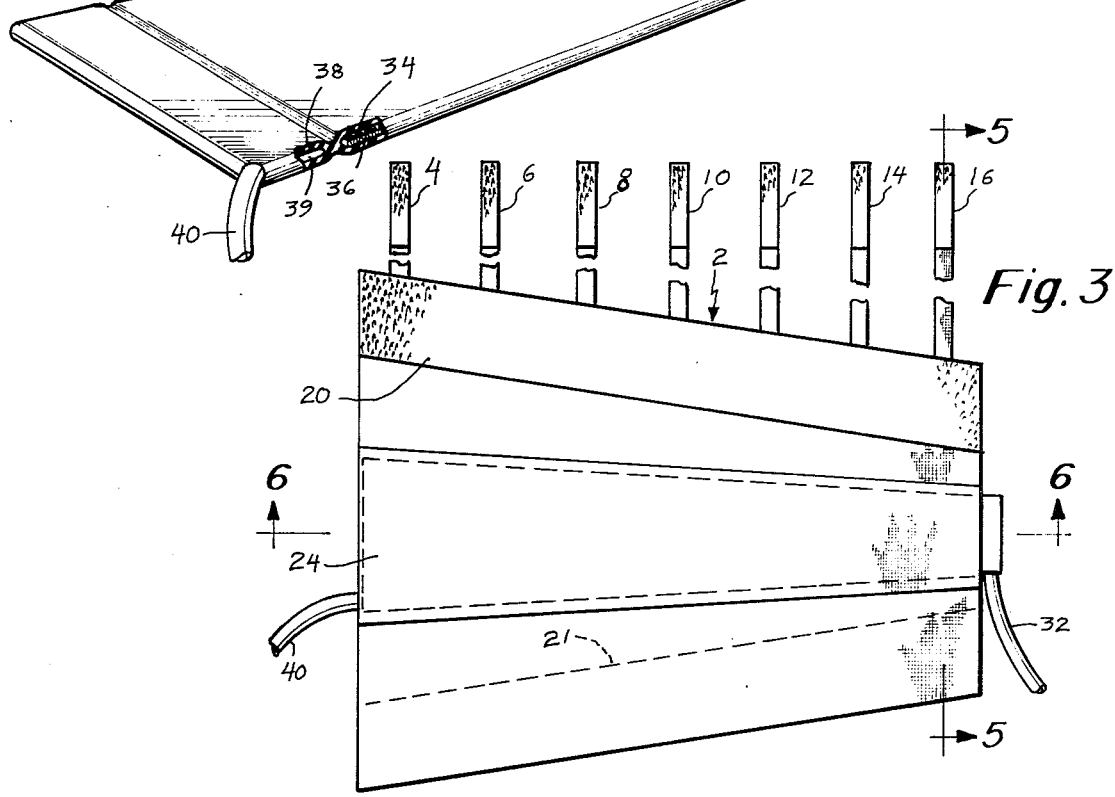
Fig. 3
Fig. 4
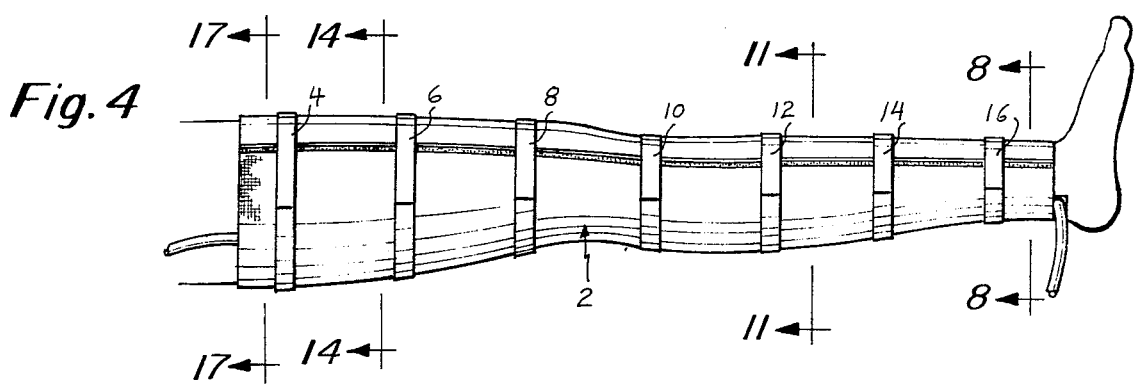

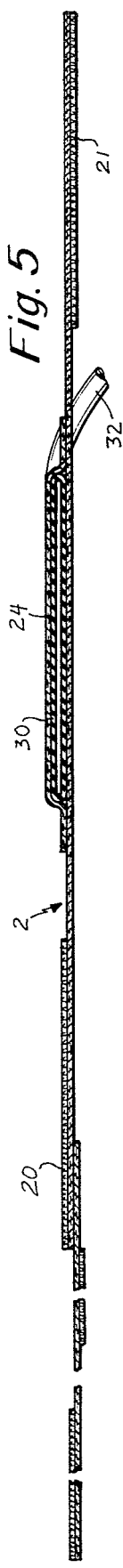
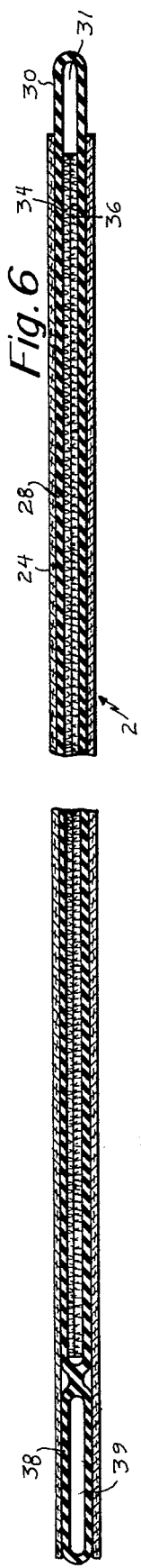
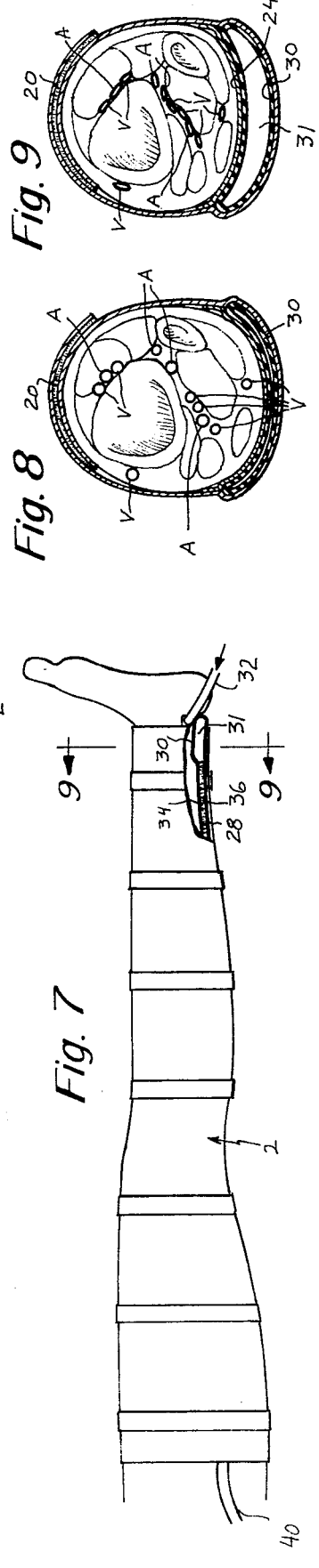
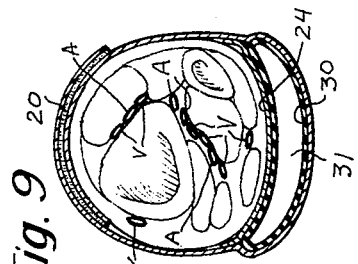
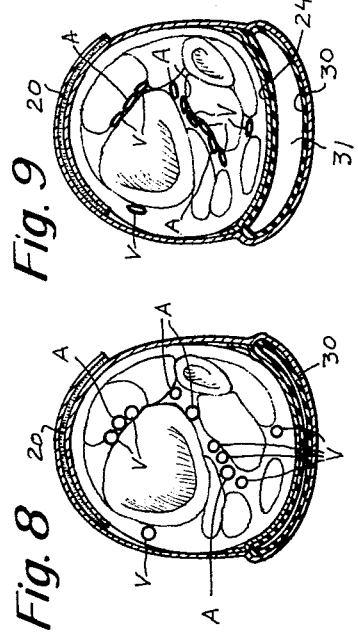
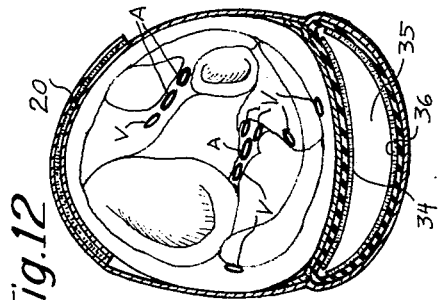
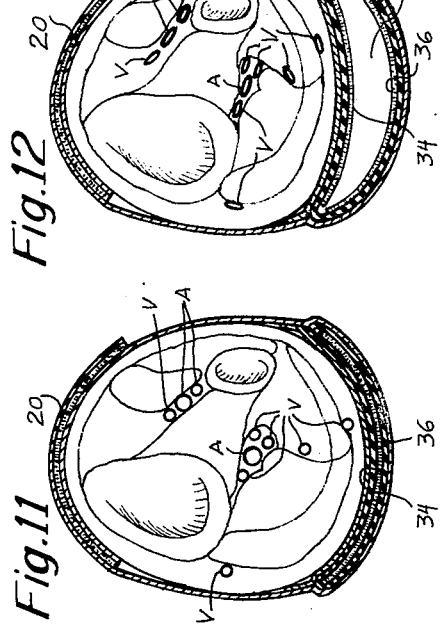

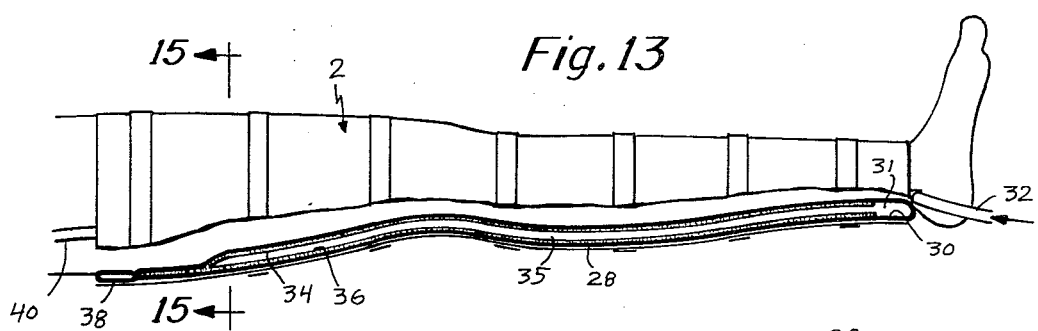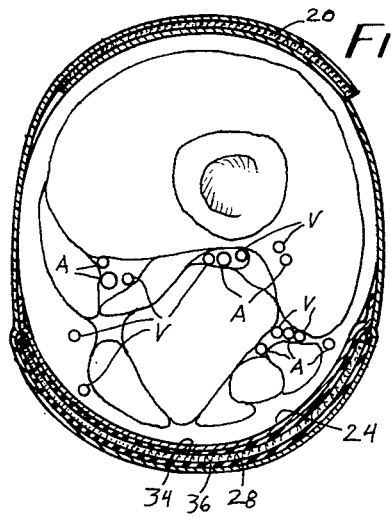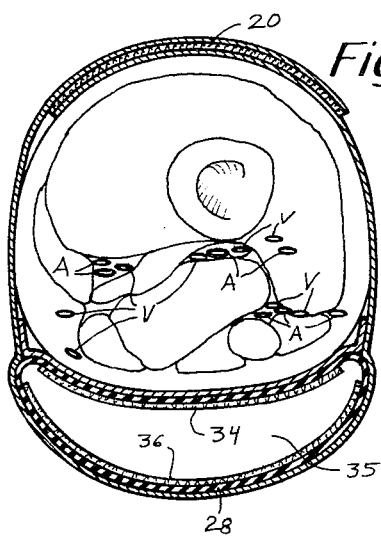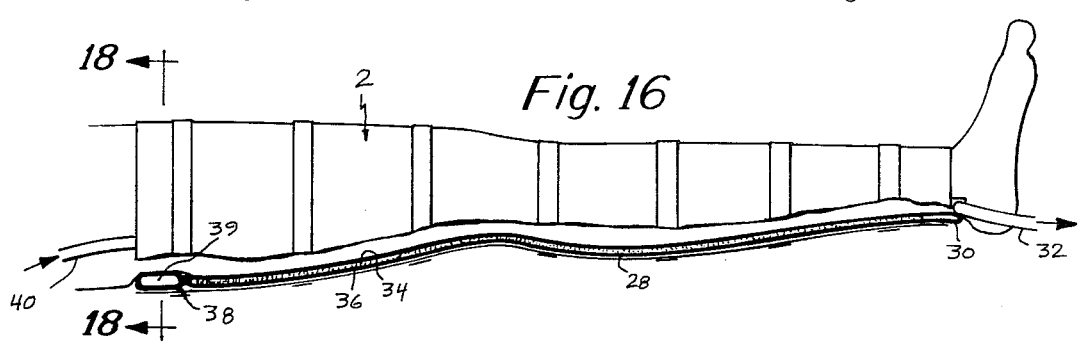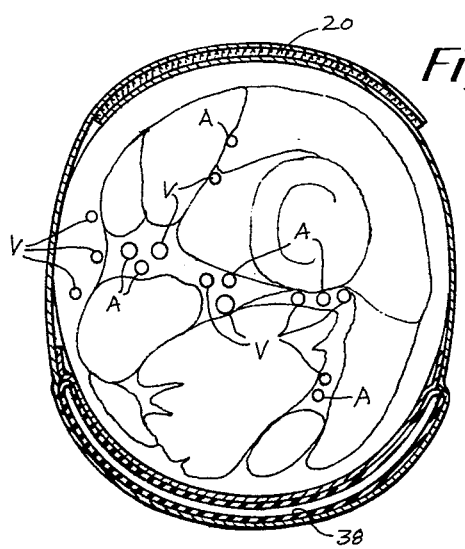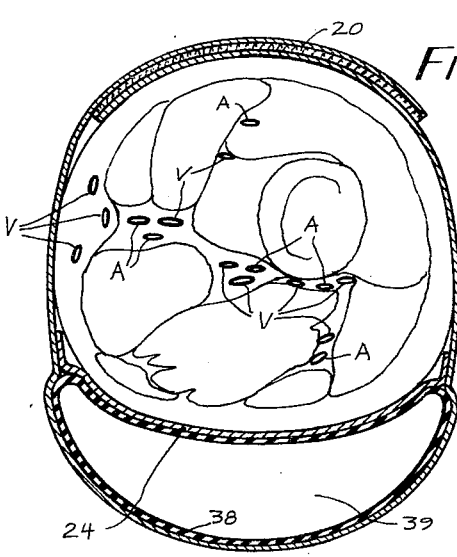

AUTO-TRANSFUSION TORNIQUET APPLIANCE AND METHOD OF UTILIZING THE SAME TO CONTROL FLOW OF BLOOD THROUGH A BLOOD VESSEL

BACKGROUND OF THE INVENTION

The use of tourniquet devices is well known in the medical profession. However, there is presently needed a better tourniquet system for controlling flow of blood in a specific manner. Approximately 30 percent of total human blood circulates in the lower extremities of the human body of any given movement. These extremities will suffer no permanent danger if they are emptied of blood and arterial circulation is occluded even for a period of time as long as 2 hours. With a traumatized patient who is in shock from marked loss of blood it is vital to restore necessary circulation in the heart, lungs, brains, and kidney. Transfusion of typed and cross-matched blood in any medical center takes 45 minutes. Transfusion of general donor blood carries a high percent of risk and yet cannot be transfused fast enough in most of the ocasions. Milking the pooled blood from lower extremities and occluding the circulation in these areas is a very fast and safe approach which not only increases the effective circulation of the vital organs, but will decrease the cardiac output demand by occluding the arterial circulation in these areas. Therefore, to be able to milk the blood from a lower limb, there is needed a tourniquet system which applies pressure initially around the ankle region and then increases the pressure so as to continue building up progressively greater pressures gradually from the ankle to the upper thigh. In the art it has been proposed to utilize inflatable bladders for displacing blood as disclosed in U.S. Pat. No. 3,454,010 which discloses an inflatable wrapper member designed to be applied in a spiraling arrangement around the leg of a patient.

SUMMARIZATION OF THE INVENTION

The present invention relates to an improved tourniquet apparatus and is concerned with means built in the tourniquet apparatus for providing a selective control of pressure not heretofore realized in the art. It is a chief object of the invention to provide a tourniquet system which can be effectively utilized on a patient to exert pressure at the angle region of a desired intensity. It is a further object of the invention to devise a means of increasing pressure from the angle region progressively upwardly along the leg towards the thigh in a controlled manner in order that veins and arteries may be substantially collapsed and a desired displacement of blood rapidly carried out. It is still another object of the invention to provide tourniquet means in the apparatus which can be instantly clamped around the upper thigh region to prevent a return flow of blood to the lower leg while desired operative procedures are carried out.

With these objectives in mind, I have devised a tourniquet apparatus which includes a wrapper member and means for detachably securing the wrapper around the leg of the patient. Included in the wrapper are inflatable chamber members which can be selectively inflated to exert localized pressure in a controlled manner. Initially, pressure is exerted at the ankle region by inflating a chamber by a rubber tubing which is received in a wrapper and provides a means for connecting with a source of compressed air. A second chamber communicating with the first chamber consists of a rubber-like material yieldably held together by attached Velcro surfaces. These layers in response to gradually increasing pressure in the first chamber start to separate with the Velcro surfaces being forced apart from one another in a progressive manner, whereby pressure is distributed up along the leg. In combination with the two chambers described, I further provide a third chamber comprising a rubber tube which is separated from the Velcro layers and is located at the upper end of the wrapping and is in a position to clamp around the layers of the thigh to prevent a return flow of blood until a desired operative procedure has been carried out.

BRIEF DESCRIPTION OF THE DRAWINGS

FIG. 1 is a perspective view illustrating the tourniquet wrapper of the invention with edges engaged in overlapping relation and secured by retaining straps;

FIG. 2 is another perspective view illustrating a bladder component normally insertable in the wrapper and indicating in cross section three inflatable chamber portions;

FIG. 3 is a view showing the wrapper unfolded and the bladder component indicated therein in dotted lines;

FIG. 4 is a side elevational view showing the tourniquet apparatus engaged around the leg of a patient before pressure is applied;

FIG. 5 is a cross section taken on the line 5—5 of FIG. 2;

FIG. 6 is a cross section taken on the line 6—6 of FIG. 2;

FIG. 7 is an elevational view illustrating the tourniquet apparatus in one operative position with pressure having been exerted in the lower chamber of the bladder;

FIG. 8 is a cross section taken on the line 8—8 of FIG. 4;

FIG. 9 is a cross section taken on the line 9—9 of FIG. 7;

FIG. 10 is another elevational similar to FIG. 7, but showing in cross section portions of an intermediate chamber whose Velcro sufaces have been forced apart by increased pressure;

FIG. 11 is a cross section taken on the line 11—11 of FIG. 4;

FIG. 12 is a cross section taken on the line 12—12 of FIG. 10;

FIG. 13 is a view similar to FIGS. 11 and 10, but showing Velcro surfaces separated throughout their length;

FIG. 14 is a cross section taken on the line 14—14 of FIG. 4;

FIG. 15 is a cross section taken on the line 15—15 of FIG. 13;

FIG. 16 is a view similar to FIGS. 7, 10, and 13 and with the third chamber portion fully inflated to exert a clamping action;

FIG. 17 is a cross section taken on the line 17—17 of FIG. 4;

FIG. 18 is a cross section taken on the line 18—18 of FIG. 6.

DETAILED DESCRIPTION OF THE INVENTION

The principal parts of the apparatus of the invention include a wrapper member, means for detachably securing the wrapper around the leg of a patient, and a bladder component insertable in a pocket formed in the wrapper and constructed with three chamber sections.

A source of compressed air is required and may be of conventional nature, and valve means for connecting with the source of compressed air is provided at opposite ends of the bladder component.

Considering these parts in greater detail, attention is directed to FIGS. 1, 2, and 3 in which numeral 2 denotes a wrapper member. In one preferred form, the wrapper member may consist of a non-stretchable fabric. Other sheet materials may be employed. As shown in FIG. 3, the wrapper may be of a tapered shape and may be of a length suitable for engaging around a patient's leg including the ankle, lower leg, and thigh portions as suggested in FIG. 4.

Along one edge of the wrapper of number 2 are fastened a plurality of retaining straps 4, 6, 8, 10, 12, 14 and 16. The straps are made of fabric, plastic, or other sheet material and at their undersides are provided with Velcro fastening surfaces.

Also provided along the opposite sides of the wrapper 2 are Velcro surfaces 20 and 21 which are best shown in FIGS. 1 and 3. These surfaces are designed to overlap one another as shown in FIG. 1 when the wrapper 2 is placed around the leg of the patient as suggested in FIG. 4. When thus arranged, in overlapping relationship and engaged against one another, the Velcro surfaces function to secure the wrapper firmly around the leg of the patient and this holding action is reinforced by the retaining straps and therefore the wrapper cannot be expanded or stretched.

Along an intermediate portion of the wrapper number 2 is located a strip of fabric or other suitable sheet material indicated in the drawing by numeral 24. This strip of material is secured to the wrapper along its edges to form a pocket 26 as shown in FIG. 1. Received in pocket 26 is the bladder component of the invention indicated by numeral 28 and shown removed from the pocket 26 in FIG. 2. The bladder component is made up of a rubberlike material and is constructed with three chamber sections into which compressed air may be selectively introduced. A first chamber section consists in an inflatable rubber tubing section denoted by the numeral 30 and indicated in FIG. 2 and also in FIGS. 5 and 6. A valve connection 32 connects this tubular section 30 with a suitable source of compressed air. Within the tubing is a space 31. The inflatable tubular part 30 merges with the rubberlike material of which the bladder component 28 is made and this merged relationship is most clearly shown at the right hand side of FIG. 6.

A second chamber section is comprised by layers of Velcro fastening material 34 and 36 which are located on respective inner surfaces of the rubberlike material of the bladder component 28 as may be more clearly seen from an inspection of FIG. 6, and which function to yieldably hold the bladder sides together. Thus it will be noted that the inflatable tubing 30 defines the space 31 earlier noted and this space is in communication with the inner surfaces of the bladder component surfaces 34 and 36. As a result, compressed air introduced into the space 31 of tubing 30 exerts a pressure and when the pressure is of a sufficient magnitude, it starts to force apart a bladder member 28 and also forces apart and disengages Velcro 34 and 36 in a progressive manner. This provides an elongated space 35 as shown in FIG. 13.

A third chamber section is located at the larger end of the wrapper member and consists of an inflatable tubing 38 which defines a space 39 in which compressed air may be contained. As shown in FIGS. 2 and 6 the inflatable tubing 38 constitutes an extension of the bladder 28, but is separated from the chamber 35 of the bladder by means of a solid joining wall 41. This joining wall 41 not only forms a separate chamber, but also limits the space which is opened when the Velcro surfaces 34 and 36 are forced apart as may be readily seen in 36.

In applying the tourniquet apparatus described, the wrapper 2 is spread open as shown in FIG. 3 and the leg of the patient is placed on the wrapper in a centrally disposed position. Thereafter, the Velcro surfaces are wrapped around the leg and firmly engaged with the retaining straps being secured over the overlapping portions as shown in FIG. 1. This procedure requires only a few seconds to carry out and is an important feature in dealing with emergency cases.

With the wrapper member thus firmly secured in place, compressed air is introduced into the flatable tubing 30 through connecting part 32 and pressure is raised to a value as high as 80 mm Hg and this pressure is exerted for a short interval during which blood in the veins and arteries of the ankle is forced upwardly and portions of these veins and arteries are collapsed as suggested in FIG. 7.

As pressure is continued in the tubing 30, the compressed air starts to move between the Velcro surfaces 34 and 36 and these parts are gradually forced apart from one another to assume an open portion as shown in FIG. 10. As this separation of the Velcro surfaces takes place, pressure is gradually applied along the entire lower leg to cause a progressive displacement of blood from arteries and veins in this region. FIG. 11 illustrates the veins and arteries in a collapsed position with blood having been forced upwardly toward the thigh.

As pressure continues to be applied increasing quantities of blood in the leg are forced upwardly through the veins and arteries with Velcro surfaces 34 and 36 becoming separated into a position such as that suggested in FIGS. 13 and 14.

When a desired pressurization has been carried out by the bladder sections described, in a very short interval of time, an independent flow of compressed air is lead into the inflatable tubing 38 and pressure is rapidly increased in the space 39 to an intensity as high as 300 mm Hg. This almost instantly clamps the veins and arteries in the thigh into a collapsed position to thereby prevent a return flow of blood during a period in which a desired operative procedure is to be carried out. This third pressure application is illustrated in FIG. 16, and FIGS. 17 and 18 illustrative arteries and veins before and after pressure is applied.

It will be seen that the tourniquet apparatus of the invention provides a rapid and safe means of moving blood from the limbs into those portions of the body where vital organs are present. This increases the effective circulating blood and decreases the cardiac output demand. In a typical usage, the appliance may be put in place and activated to a desired point in a very short time interval of less than one minute. It should also be observed that the apparatus can readily be manufactured and can be used many times.

In a preferred application of the tourniquet it may be desired to lower pressure in the chambers 31 and 35 and deflate the bladder portions 28 and 30 as soon as chamber 38 is inflated. This provides for treating an injury in the lower leg.

I claim:

1. An improved tourniquet apparatus for controlling flow of blood in a patient's body, said apparatus including a flexible, substantially non-stretchable wrapper member engageable around a limb of the patient's body and inflatable means for selectively exerting pressure along the limb to displace blood therefrom, said inflatable means consisting in a bladder supported inside the wrapper member and having intermediate portions yieldably secured together by Velcro surfaces.

2. An improved tourniquet apparatus for controlling flow of blood in a patient's body, said apparatus including a flexible, substantially non-stretchable wrapper member engageable around a limb of the patient's body, inflatable means for selectively exerting pressure along the limb to displace blood therefrom, said inflatable means consisting in a bladder supported inside the wrapper member and being formed with a plurality of chamber sections, and one of the chamber sections having inner portions yieldably secured together by Velcro surfaces.

3. Method of controlling flow of blood in the body of a patient, said method including the steps of exerting a localized pressure on a limb of the patient's body to induce displacement of blood out of veins and arteries, thereafter applying pressure upwardly along the limb to gradually displace blood out of the limb into the trunk of the patient's body, said pressure being applied progressively along the said limb by yieldably containing inflatable layers together with engaged Velcro surfaces and gradually forcing the engaged Velcro surfaces into separated relationship to one another.

4. An improved tourniquet apparatus for controlling flow of blood in a patient's body, said apparatus including a flexible, substantially non-stretchable wrapper member engageable around a limb of the patient's body and inflatable means for selectively exerting pressure along the limb to displace blood therefrom, said inflatable means including a bladder component supported inside the wrapper member and being formed with successive inflatable chambers, one of said inflatable chambers being located in the wrapper in a position to exert pressure around the ankle portion of the said patient's limb a second inflatable chamber having portions yieldably secured together by Velcro surfaces, said portions being separable in response to increase in pressure in the said first chamber to progressively exert pressure along intermediate portions of the patient's limb and to force a flow of blood upwardly along the knee portion of the patient's limb, and a third inflatable chamber located in the wrapper in a position to exert pressure independently of the first and second chambers around the thigh portion of the patient's limb to prevent a return flow of blood along the patient's limb.

* * * * *